(12) United States Patent  (10) Patent No.: US 8,506,547 B2
Sharratt et al.  (45) Date of Patent: Aug. 13, 2013

(54) DEVICE AND METHOD FOR TRANSFERRING FLUIDS WITHIN A SURGICAL ENVIRONMENT

(75) Inventors: Todd William Sharratt, Stillwater, MN (US); Kenneth Mitchell Goodman, Minneapolis, MN (US); Curtis H. Miller, Inver Grove Heights, MN (US)

(73) Assignee: Nordson Corporation, Westlake, OH (US)

( * ) Notice: Subject to any disclaimer, the term of this patent is extended or adjusted under 35 U.S.C. 154(b) by 896 days.

(21) Appl. No.: 12/510,676

(22) Filed: Jul. 28, 2009

(65) Prior Publication Data

US 2010/0022974 A1  Jan. 28, 2010

Related U.S. Application Data

(60) Provisional application No. 61/084,080, filed on Jul. 28, 2008.

(51) Int. Cl.
*A61B 19/00* (2006.01)
(52) U.S. Cl.
USPC .......................................... 604/403; 604/533
(58) Field of Classification Search
USPC ................. 604/403, 411, 412, 414, 533–535
See application file for complete search history.

(56) References Cited

U.S. PATENT DOCUMENTS 6,582,415 B1 * 6/2003 Fowles et al. ................. 604/413
2002/0087141 A1 * 7/2002 Zinger et al. .................. 604/414

* cited by examiner

*Primary Examiner* — Melanie Hand
(74) *Attorney, Agent, or Firm* — Wood, Herron & Evans, L.L.P.

(57) ABSTRACT

A method and device for transferring fluids from a non-sterile field to a sterile field within a surgical environment includes utilizing a device that includes a main body having a first inlet port that is in communication with a first outlet port. Fluid is taken from the patient, typically with a sterile syringe and transferred to the non-sterile field where the fluid is processed. The processed fluid is then drawn into another syringe in the non-sterile field and a distal end of the first syringe is place within the inlet port of the sterile main body. A distal end of a second sterile syringe is inserted into the outlet port, where the distal ends of the sterile syringe and the non-sterile syringe do not make contact. As a plunger is forced into a chamber of the first non-sterile syringe to force the fluid out of the first syringe, the plunger of the second sterile syringe is retracted such that a chamber in the second syringe has a sufficient volume to store the processed liquid. Since the first non-sterile syringe and the second sterile syringe do not make contact during the transfer of the processed fluid, the sterile field is maintained and the fluid can be utilized in the surgical procedure.

13 Claims, 15 Drawing Sheets

DEVICE AND METHOD FOR TRANSFERRING FLUIDS WITHIN A SURGICAL ENVIRONMENT

CROSS REFERENCE TO RELATED APPLICATION

The present application claims the benefit of U.S. Provisional Patent Application Ser. No. 61/084,080 that was filed on Jul. 28, 2008, the contents of which are incorporated by reference in its entirety.

FIELD OF THE INVENTION

The present invention relates to a device and method of transferring fluids in a surgical environment. More particularly, the present invention relates to a method and device for transferring fluids from a non-sterile field in the surgical environment to a sterile field within the surgical environment while maintaining the sterility of the sterile field.

BACKGROUND OF THE INVENTION

A surgical environment, such as an operating room, is typically segregated into a sterile field and a non-sterile field. The segregation of the operating room, including personnel, between the sterile field and the non-sterile field is necessary to minimize the likelihood of infection in the patient as the result of the surgical procedure.

The sterile field and the non-sterile field are not defined by physical boundaries, but rather by surfaces that are sterile and surfaces that are not sterile. Sterile surfaces are aseptic and free of potential infectious organisms. Non-sterile surfaces in an operating room are very clean. However, sterilizing procedures which are time consuming and costly have not been utilized on the non-sterile surfaces. Therefore, surfaces that have no been subjected to sterilizing procedures are considered to be in the non-sterile field.

The sterile field includes all surfaces that have been deliberately prepared to be sterile. A non-exhaustive list of sterile surfaces include the prepared surgical site on the body of the patient, the drape that is positioned over the patient's body and around the surgical site, the surfaces from the chest to the waist of the personnel in the sterile field as well as the surfaces from the elbows to the tips of the fingers provided the personnel have been scrubbed according the prescribed protocol, sterilized surgical gowns, sterilized gloves and sterilized surgical instruments. Other surfaces may also be prepared as sterile.

Other surfaces, while very clean, are not considered sterile, and in order to maintain the sterile field, non-sterile surfaces are not allowed to contact surfaces in the sterile field. Therefore, great care must be taken to ensure the sterility of the sterile field.

In some surgical procedures fluid, such as blood, is taken from the patient and processed in the non-sterile field. The transfer of the fluid from the sterile field to the non-sterile field can be achieved by handing a surgical instrument such as a syringe from personnel in the sterile field to personnel in the non-sterile field by refraining from making hand to hand contact. However, the transfer of the fluid from the non-sterile field to the sterile field is difficult to achieve, as the fluid must be transferred from the non-sterile surgical instrument to a sterile surgical instrument without contaminating the sterile field.

SUMMARY OF THE INVENTION

The present invention includes a method and device for transferring fluids from a non-sterile field to a sterile field within a surgical environment, such as an operating room. The device includes a main body having a first inlet port that is in fluid communication with a first outlet port. The device is typically in a sterile field. Fluid is taken from the patient, typically with a sterile syringe and transferred to the non-sterile field where the fluid is processed. Once the syringe is transferred to the non-sterile field from the sterile, the syringe is no longer considered sterile. The processed fluid is then drawn into another syringe in the non-sterile field and a distal end of the first syringe is place within the inlet port of the sterile main body. A distal end of a second sterile syringe is inserted into the outlet port, where the distal ends of the sterile syringe and the non-sterile syringe do not make contact. As a plunger is forced into a chamber of the first non-sterile syringe to force the fluid out of the first syringe, the plunger of the second sterile syringe is retracted such that a chamber in the second syringe has a sufficient volume to store the processed liquid. Since the first non-sterile syringe and the second sterile syringe do not make contact during the transfer of the processed fluid, the sterile field is maintained and the fluid can be utilized in the surgical procedure.

DETAILED DESCRIPTION OF ILLUSTRATIVE EMBODIMENTS

Figure 1:
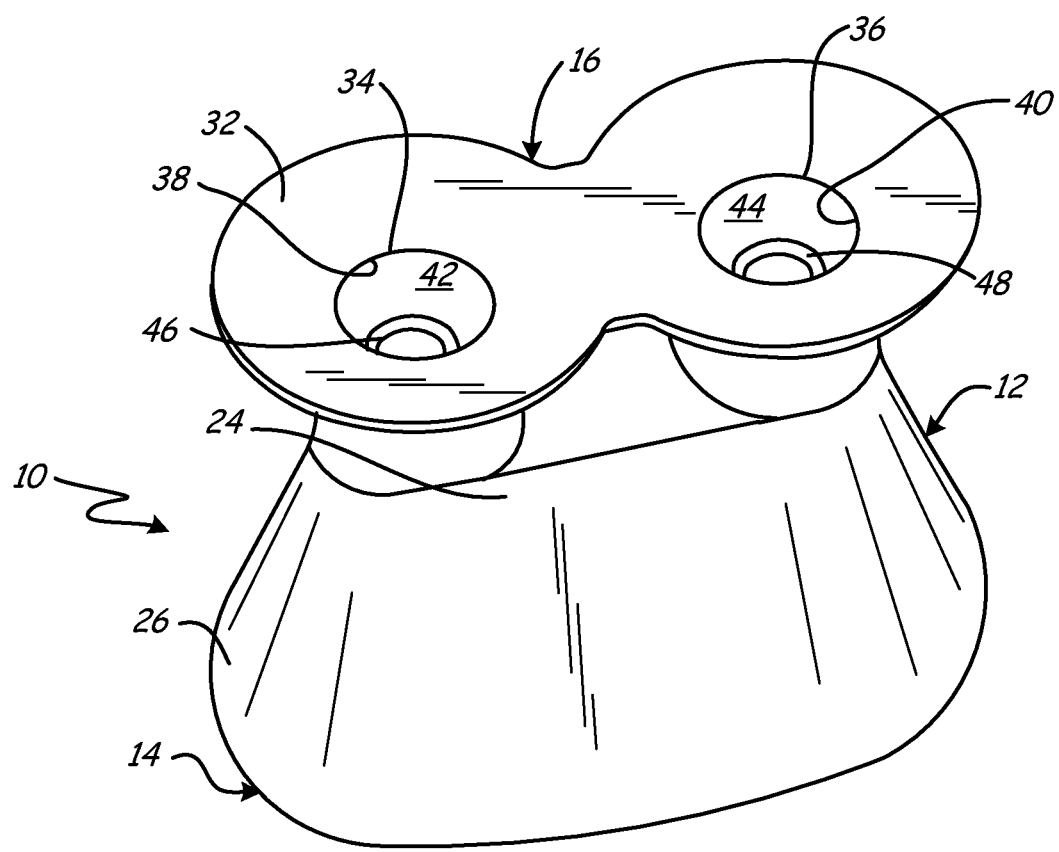
FIG. 1 is a perspective view of the sterile fluid transfer device as viewed from the bottom.

The present invention relates to a method, a device and a kit for transferring fluids from a non-sterile field to a sterile field in a surgical environment such as an operating room. A fluid transfer device is generally illustrated in FIG. 1 at 10. The device 10 is utilized along with at least two syringes, where the device 10 and the syringes can be packaged individually or together in a kit with the device 10. The device 10 and the syringes are sterilized and are a portion of the sterile field when initially placed in the operating room.

Figure 2:
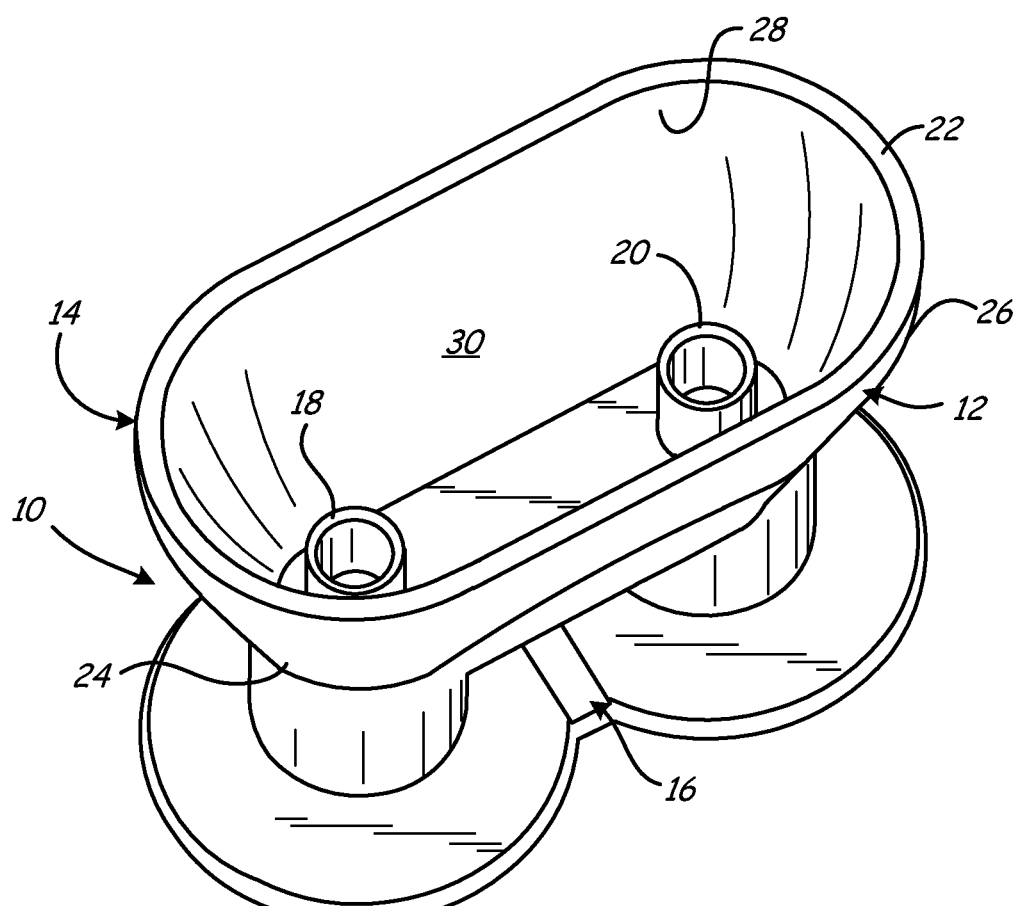
FIG. 2 is a perspective view of the sterile fluid transfer device as viewed from the top.

Referring to FIGS. 1 and 2, the sterile fluid transfer device 10 is utilized to transfer one or more fluids from a non-sterile field to the sterile field in an operating room. Typically, the patient's blood or blood component and another fluid such as a hardener are transferred from the non-sterile field to the sterile field. The two fluids are typically mixed together in a spray nozzle attached to an end of a multi-chambered syringe and sprayed onto the surgical site. One typical application of two or more fluids is to applying the blood component and a hardener to stop the patient from bleeding during the surgical procedure while reducing the likelihood of an adverse reaction to the mixture because the patient's own blood is being utilized.

The device 10 includes a main body 12 having a top portion 14 and a bottom portion 16. The top portion 14 includes left and right inlet ports 18 and 20, respectively, that are sized to accept distal or discharge ends of a dual chamber syringe. While a fluid transfer device is illustrated with two inlet ports, it is also contemplated that the device can be utilized to transfer only one fluid where the device has one inlet port and one outlet port or more than two fluids by increasing the number of inlet ports and outlet ports to the number of desired fluids to be transferred.

The top portion 14 includes a continuous top edge 22 having substantially straight, parallel side edges joined by opposing arcuate ends. A continuous sidewall 26 extends from the top edge 22 to a barrier wall 24 that separates the top portion 14 from the bottom portion 16. The sidewall 26 is typically tapered or slanted such that the top edge 22 is connected to a perimeter of the barrier wall 24.

Figure 3:
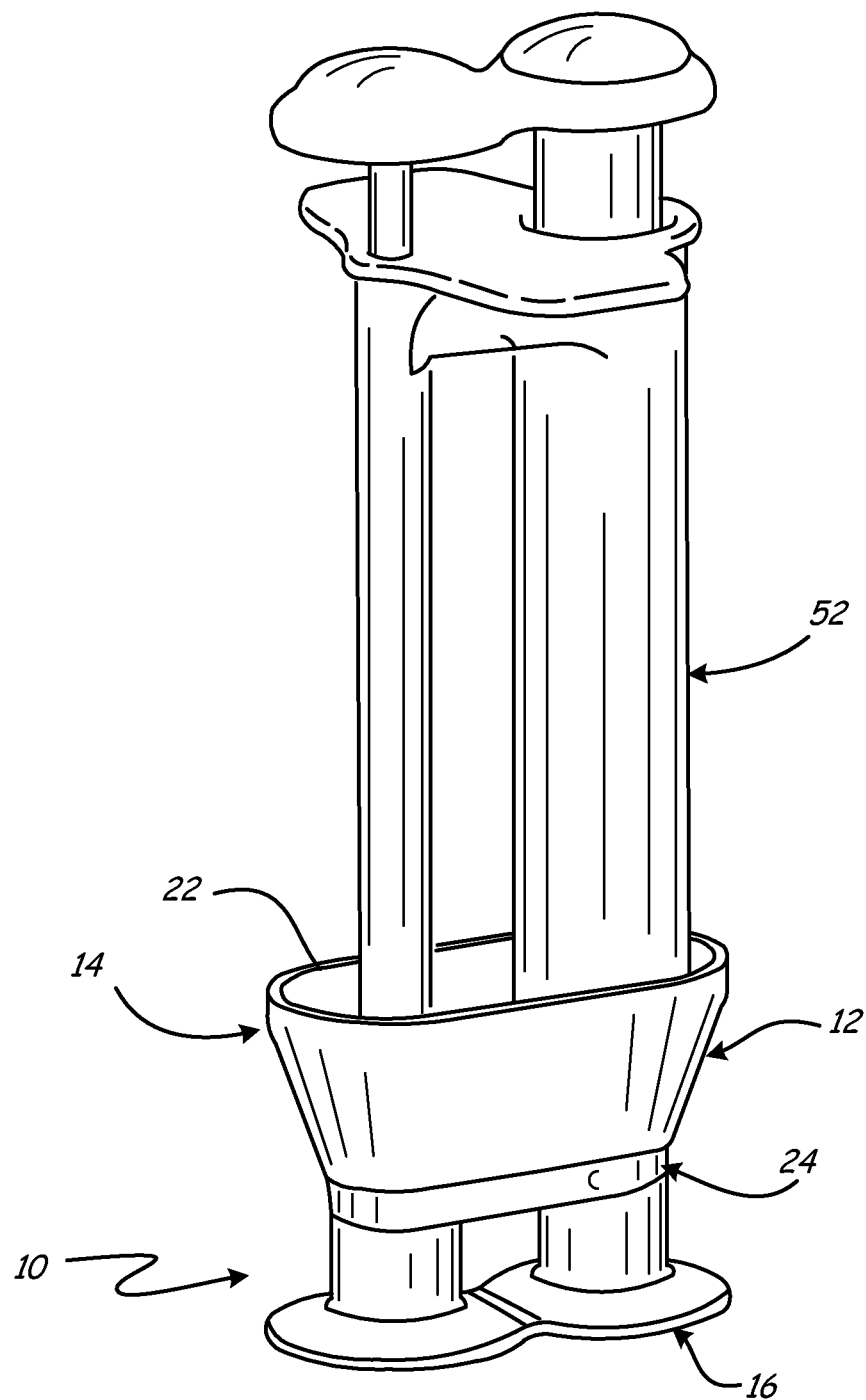
FIG. 3 is a perspective view a sterile fluid transfer device with a dual chamber syringe engaged with inlet ports in the fluid transfer device.
Figure 4:
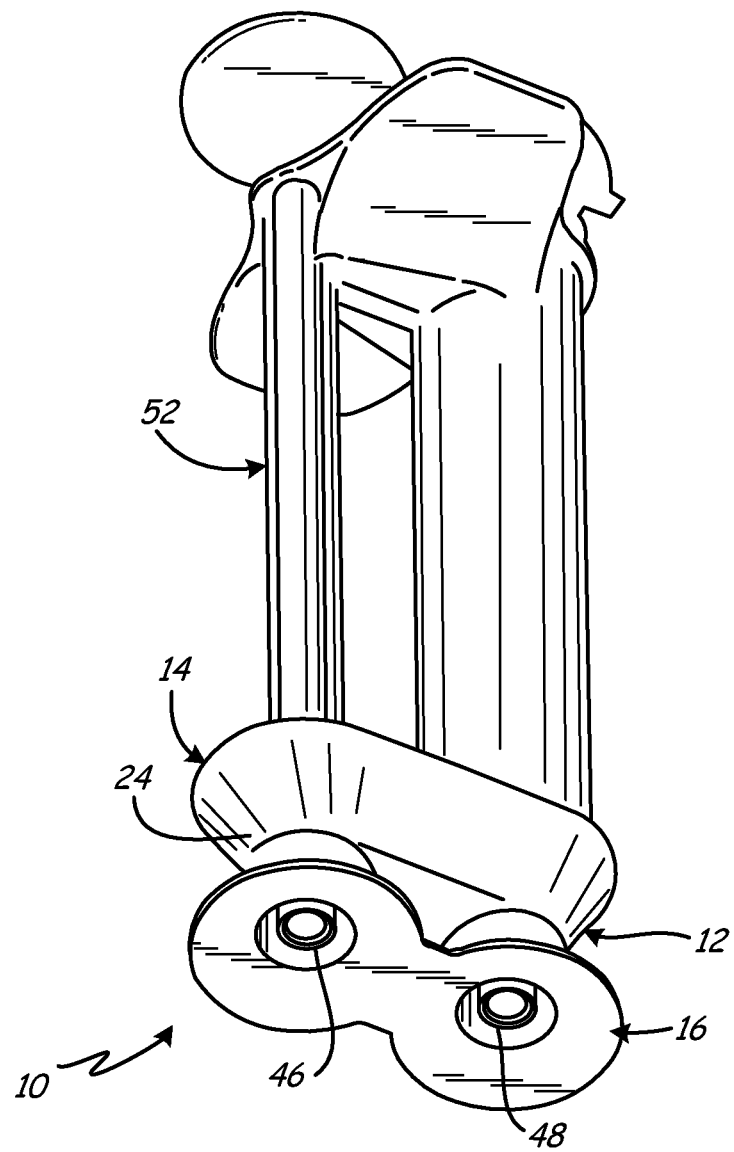
FIG. 4 is another perspective view of the sterile fluid transfer device with a dual chamber syringe engaged with inlet ports in the fluid transfer device.

The tapered sidewall 26 defines a cavity 30 that contains the left and right inlet ports 18 and 20, respectively. A tapered or slanted inner surface 28 of the sidewall 26 provides a wide opening into the cavity 30 for positioning a dual chamber syringe into the cavity 30. As the distance between the side walls converge, the inner surface 28 facilitates the positioning of the discharge ends the dual chamber syringe within the left and right inlet ports 18 and 20, respectively, as best illustrated in FIGS. 3 and 4 with a dual chamber syringe 52.

Referring back to FIGS. 1 and 2, the bottom portion 16 includes a substantially flat, bottom surface 32 that includes openings to left and right cavities 34 and 36, respectively. The left and right cavities 34 and 36 are separated from each other and include tapered sidewalls 38 and 40 which form frusto-conical cavities 42 and 44, all respectively. The tapered sidewalls 38 and 40 guide discharge ends of another dual chamber syringe into left and right discharge ports 46 and 48, respectively.

The left inlet port 18 is in fluid communication with the left outlet port 46 with a left through bore (not shown) that passes through the barrier wall 24. The right inlet port 20 is in fluid communication with the right outlet port 48 with a right through bore (not shown) that also passes through the barrier wall 24. The left and right through bores provide a restriction between the respective ports where the left and right through bores typically are of the same internal diameter of the discharge luers of the syringe. The restriction in the through bore minimizes the amount of fluid waste caused by spillage during transfer.

The barrier wall 24 is of a sufficient thickness such that when a sterile syringe is secured to the outlet ports 46 and 48 and a non-sterile syringe is secured to the inlet ports 18 and 20, the discharge ends of the syringes do not make contact. Since the discharge ends of the syringes do not make contact, the sterile field is maintained during and after transfer of the fluids to the sterile syrnge.

The device 10 is typically constructed of a thermoplastic material that is capable of withstanding sterilization temperatures in an autoclave. However, other materials of construction are also contemplated.

Typically, the fluids that are drawn into the dual chamber syringe are drawn into the separate chambers at different times. The plungers typically work independently from each other to draw different fluids into the syringe. The chambers of the syringe are typically sized to provide a desire ratio of each fluid. The plungers are optimally depressed into the chambers at the same time and at the same rate to provide an optimal concentration of the two sprays. Locking the plunger heads together ensures that the plungers are depressed at the same time and at the same rate which ensures the optimal concentration of each fluid is applied on the surgical site to maximize the effectiveness of the spray.

Figure 5:
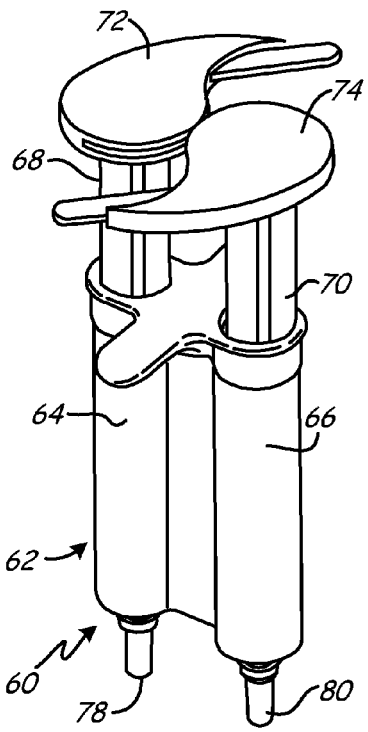
FIG. 5 is a perspective view of a dual chamber syringe having plunger heads that are disconnected from each other.
Figure 6:
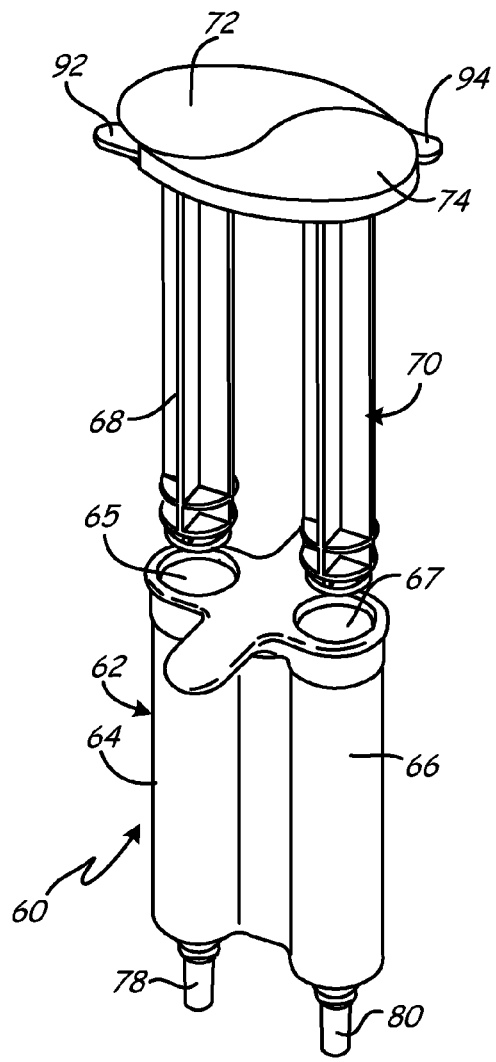
FIG. 6 is an exploded view of the dual chamber syringe having the plunger heads connected to each other.

A dual chamber syringe as best illustrated in FIGS. 5 and 6 at 60 includes the capability of locking and unlocking the plunger heads. The dual chamber syringe includes a housing 62 having a left chamber 64 and a right chamber 66. A left plunger 68 is moveably inserted into a left cavity 65 in the left chamber 64. A right plunger 70 is moveably inserted into a right cavity 67 in the right chamber 66. The left plunger 68 includes a left plunger head 72 which is attached to a top end of the left plunger 68. The right plunger 70 includes a right plunger head 74 that is attached to a top end of the right plunger 70.

The left plunger head 72 and the right plunger head 74 can be rotated such that the left and right plunger heads 72 and 74, respectively, are disconnected as best illustrated in FIG. 5 or interconnected and joined together as best illustrated in FIG. 6. While this application refers to elements in terms of left and right, depending upon how the device is viewed the directional terms may change.

Referring to FIG. 5, the left and right plungers 68 and 70 can be depressed into the left and right chambers 64 and 66 independently of each other. Referring to FIG. 6, the left and right plunger heads 72 and 74 are rotated such that the left and right plunger heads 72 and 74, respectively, are interconnected such that the left and right plungers 68 and 70 move simultaneously within the left and right chambers 64 and 66. As the left and right plungers 68 and 70 are depressed, a liquid is forced out of the left discharge nozzle 78 and a right discharge nozzle 80 extending from the bottom end of a left and right chambers 64 and 66, respectively.

Figure 8B:
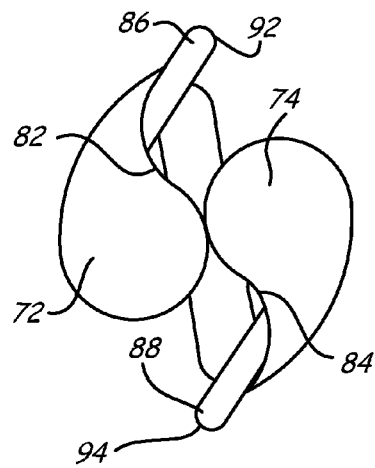
FIG. 8B is a top view of a single plunger head.
Figure 8A:
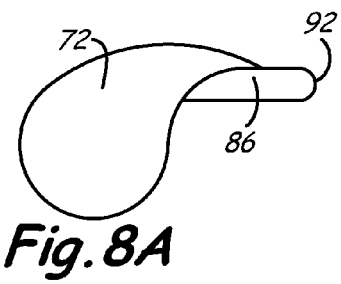
FIG. 8A is a top view of the plunger heads in a disconnected configuration.
Figure 9:
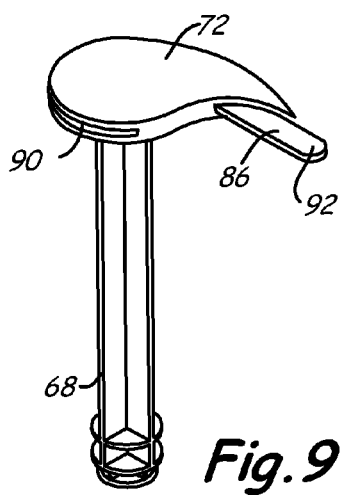
FIG. 9 is a perspective view of a plunger having a head that can be interconnected or disconnected from another plunger head.
Figure 10:
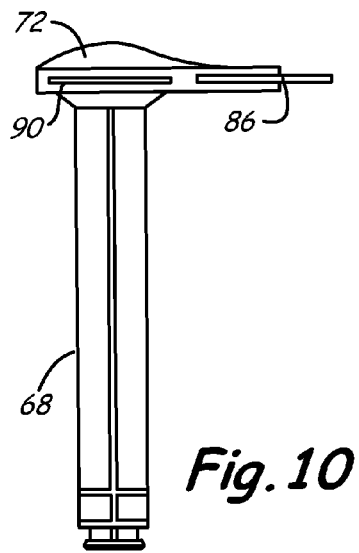
FIG. 10 is a side view of the plunger head that can be interconnected or disconnected from another plunger head.
Figure 7:
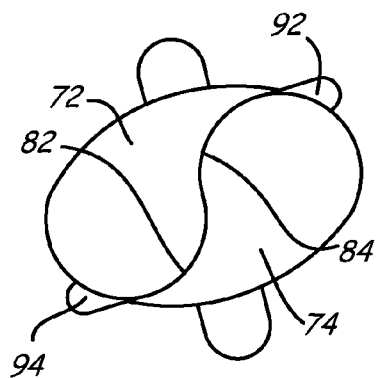
FIG. 7 is a top view of the plunger heads in an interconnected configuration.

Referring to FIGS. 7-10, the left and right plunger heads 72 and 74 include inner curved surfaces 82 and 84, respectively, which intermesh with each other to form one continuous plunger head as best illustrated in FIG. 7. The plunger heads 72 and 74 can be rotated such that the curved surfaces 82 and 84 are detached from each other such that the left and right plungers 68 and 70 can be operated independently of each other as best illustrated in FIG. 8.

A securing mechanism for the left and right plungers 68 and 70 include tabs 86 and 88 extending from the left a right heads 72 and 74 which, when rotated into a fixed position, engage a slot 90 within the other head such that when the tab 86 or 88 is positioned within the opposing slot 90, the two plunger heads 72 and 74 interconnected with each other. Typically, an end 92 and 94 of each of the tabs 86 and 88, respectively, extend out from the perimeter of the plunger heads 72 and 74 when the plunger head 72 and 74 are interconnected such that the operator can engage the ends 92 and 94 and apply manual force to the tabs 86 and 84 to rotate each tab 86 and 88 away from the heads 69 and 74 into a disconnected configuration such that the plunger heads can be operated independently from each other.

Figure 11:
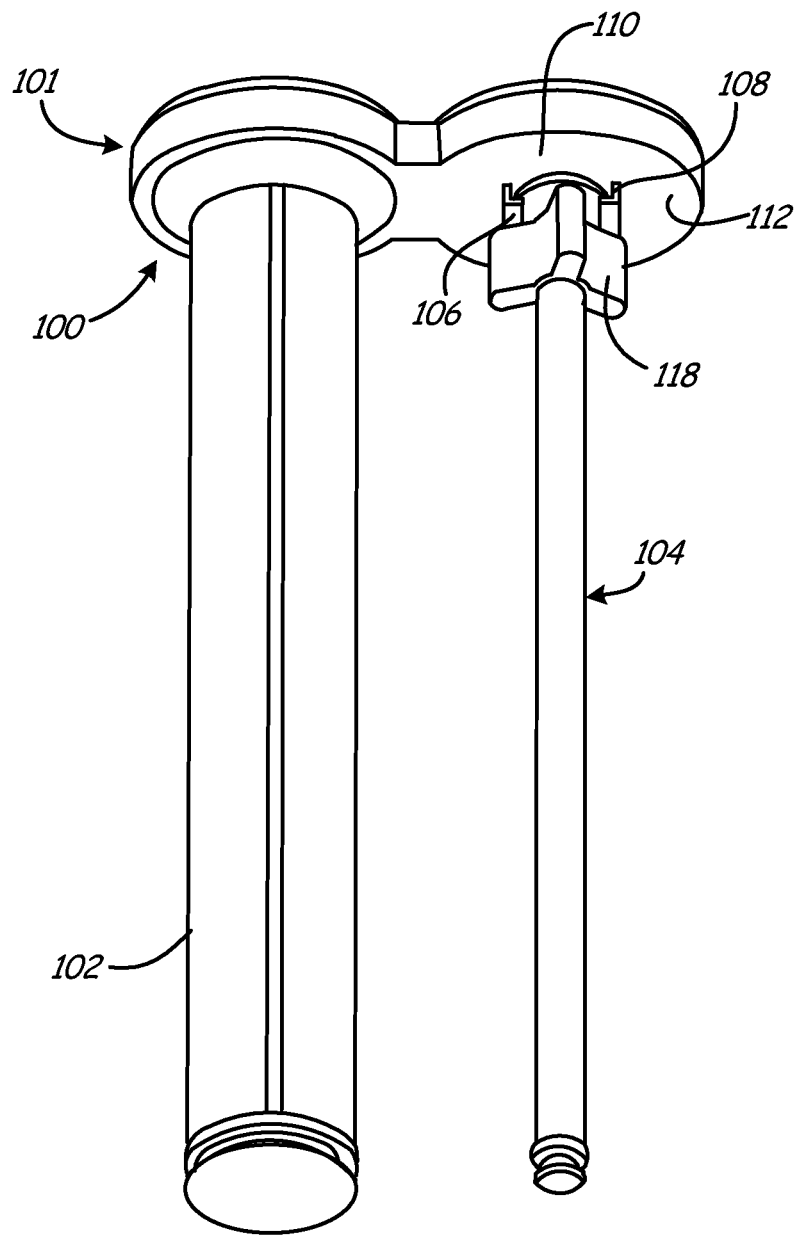
FIG. 11 is a perspective view of another configuration of a plunger head.
Figure 12:
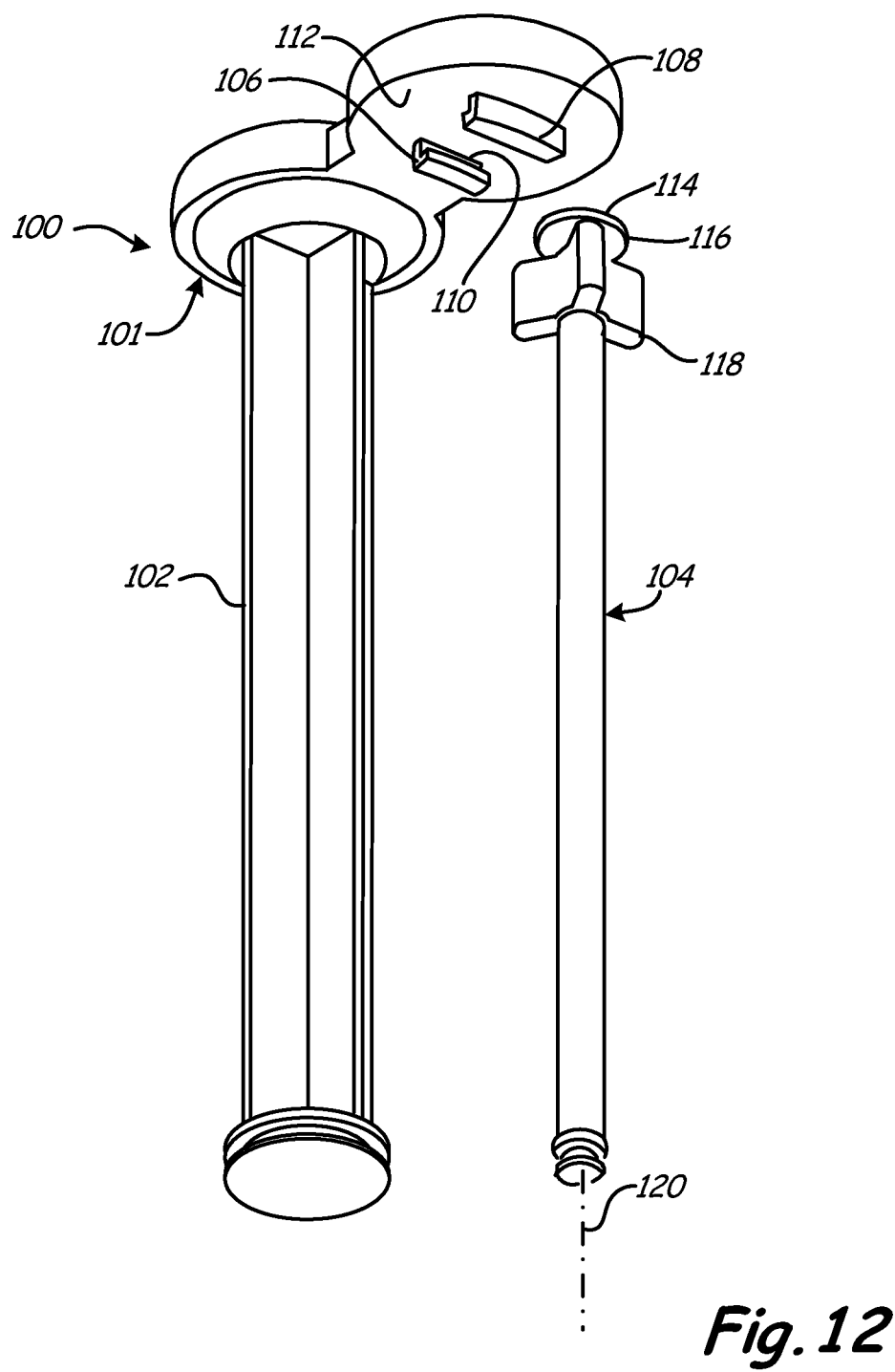
FIG. 12 is an exploded view of the plunger head illustrated in FIG. 11.

Referring to FIGS. 11 and 12, another configuration of the plunger head 100 is illustrated. The plunger head 100 includes a main body 101 having a left plunger 102 that is fixedly attached to the main body 101. The left plunger 102 may also be removably attached to the main body 101.

The right plunger 104 is removably attachable to the main body 101. The main body 101 includes left and right "L" shaped members 106 and 108 that extend from a bottom surface 112 to form a channel 110. A top end 114 of the right plunger 104 includes a disc 116 that is slidably positionable within the channel 110 where the diameter of the disc 116 is larger than the bottom entrance to the channel 110 such that the disc 116 is retained in the channel 110.

The right plunger 104 includes three protrusions 118 that extend radially from an axis 120 of the plunger 124. The protrusions 118 provide a gripping surface on the plunger 104 for securing the plunger 104 to the plunger head 100 or removing the plunger 104 from the plunger head 100. While three protrusions 118 are typical any gripping surface is contemplated.

Figure 13:
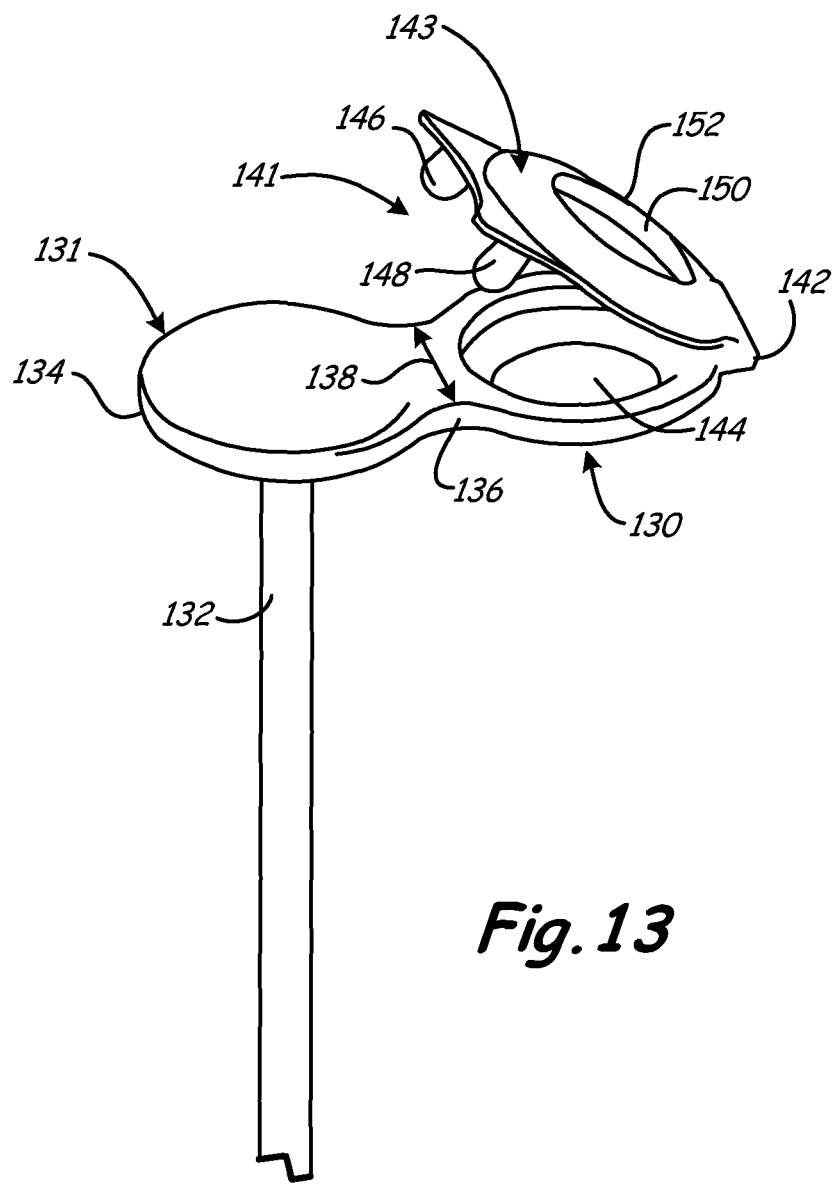
FIG. 13 is a perspective view of another plunger head.
Figure 14:
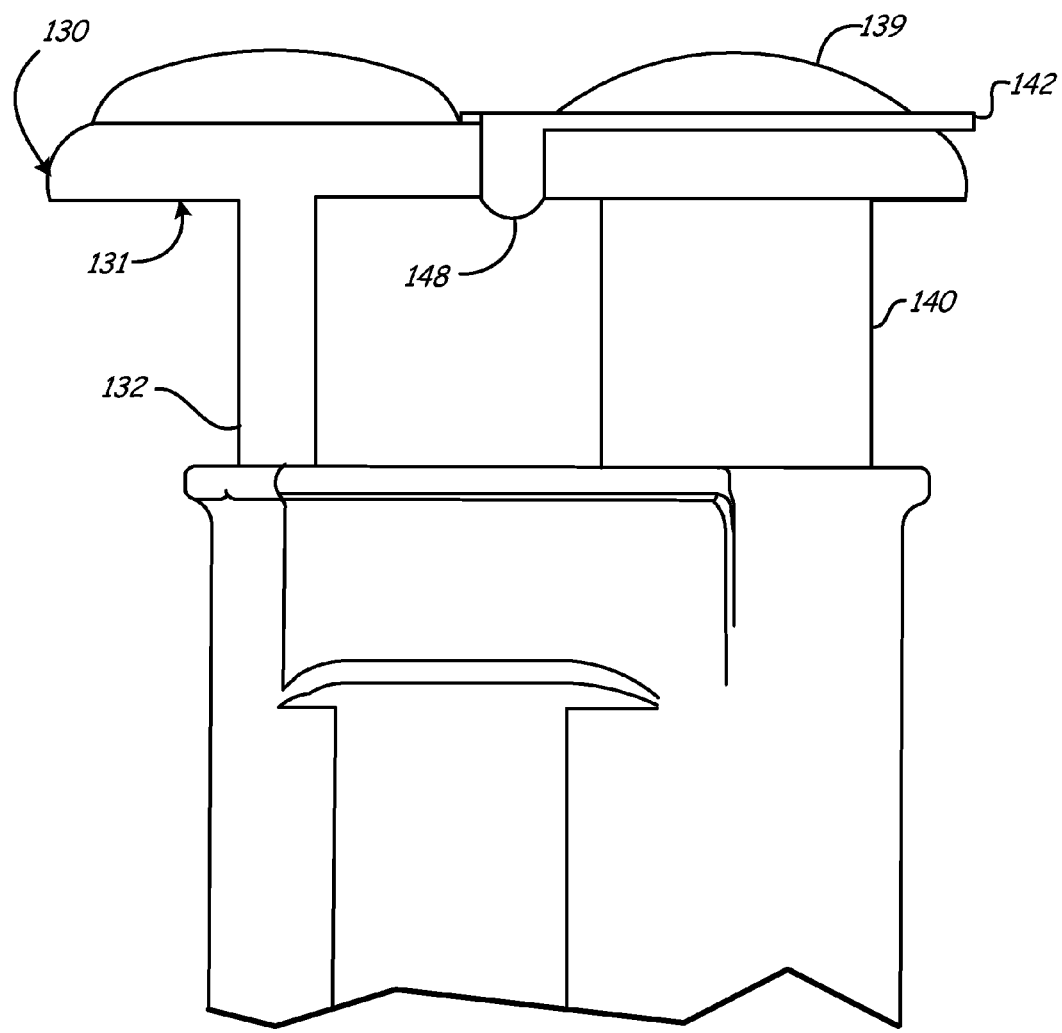
FIG. 14 is a partial side view of a syringe with the plunger head illustrated in FIG. 13.

Referring to FIGS. 13 and 14, another configuration of the plunger head 130 is illustrated. The plunger head 130 includes a main body 131 with a left plunger 132 that is fixedly attached thereto. However, the left plunger 132 may also be removably attached to the plunger head 130.

The main body 131 has an hourglass perimeter 134 where the perimeter has a concave middle portion 136 on each side that forms a narrow segment or waist 138. The main body 131 includes a right securing mechanism 141 for removably securing the right plunger 140 to the plunger head 130.

The right securing mechanism 141 includes a top flap 143 that is pivotally attached to an end of the main body 131 with a hinge 142. The top flap 143 is pivoted away from the plunger head 130 such that the right plunger 140 can be positioned through a bottom aperture 144. The head 139 of the plunger 140 has a diameter that is larger than the diameter of the aperture 144 which prevents the plunger 140 from disengaging from the plunger head 130.

With the right plunger 140 positioned through the bottom aperture 144, the flap 143 is pivoted about the hinge 142 to position the flap 143 proximate the plunger head 130. Manual force is placed upon the flap 143 to spread left and right tabs 146 and 148, respectively, apart such that the tabs 146 and 148 are positioned on opposite sides of the waist 138. The tabs 146 and 148 include ends which protrude from the surface of the tabs and engage the bottom surface of the plunger head 130 to retain the flap 143 in a secured position which retain the right plunger head 139 in a secured position.

The flap 143 includes a top aperture 150 and a concave surface 152 that conforms to the convex surface of the right plunger head 139. With the flap 143 secured to the plunger head 130, the right plunger is secured in a fixed position. The right plunger 140 can be removed by manually forcing the tabs 146 and 148 above the plunger head 130 and pivoting the flap 143 about the hinge 142.

Figure 15:
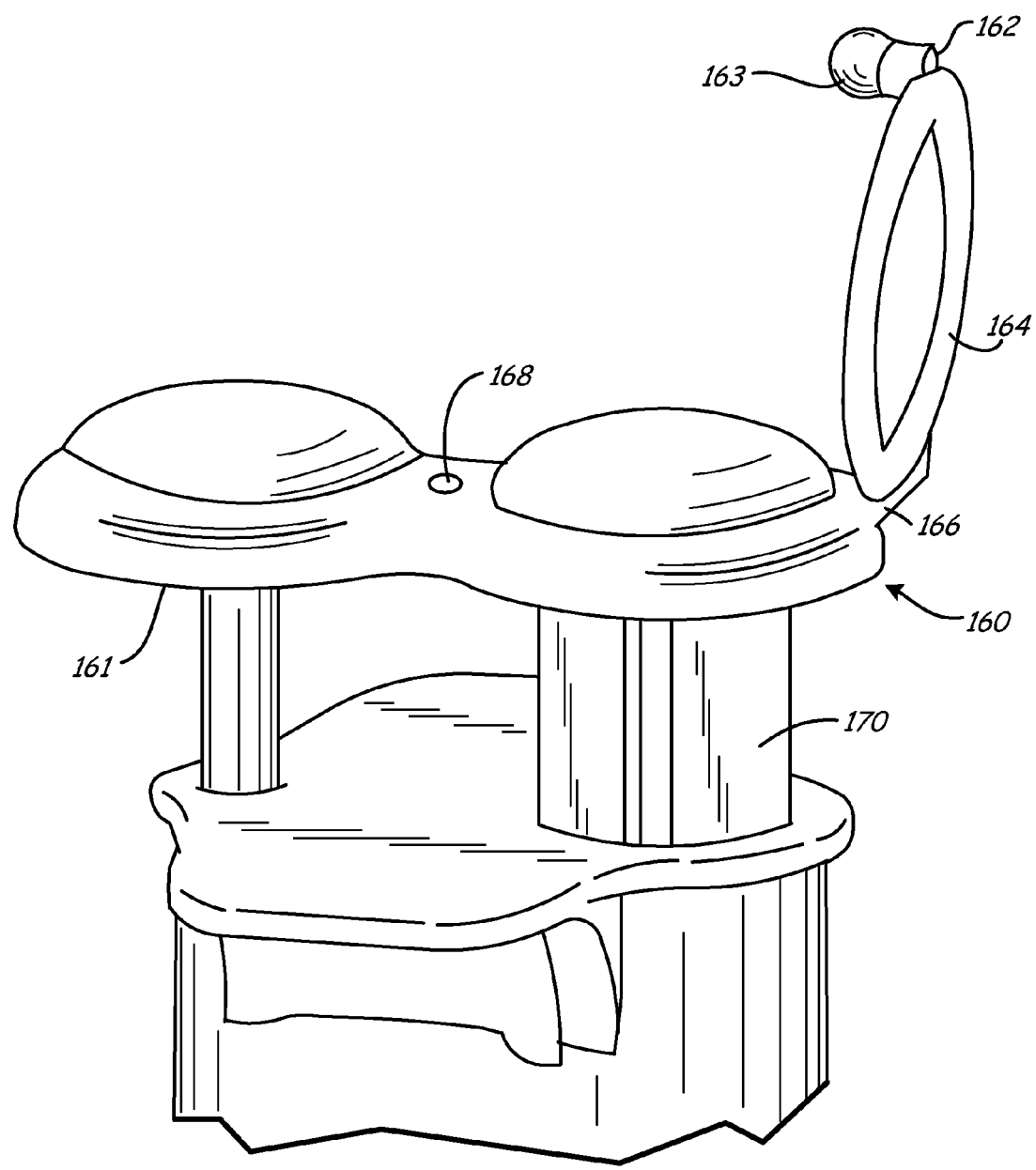
FIG. 15 is a partial perspective view of a syringe with another plunger head.
Figure 16:
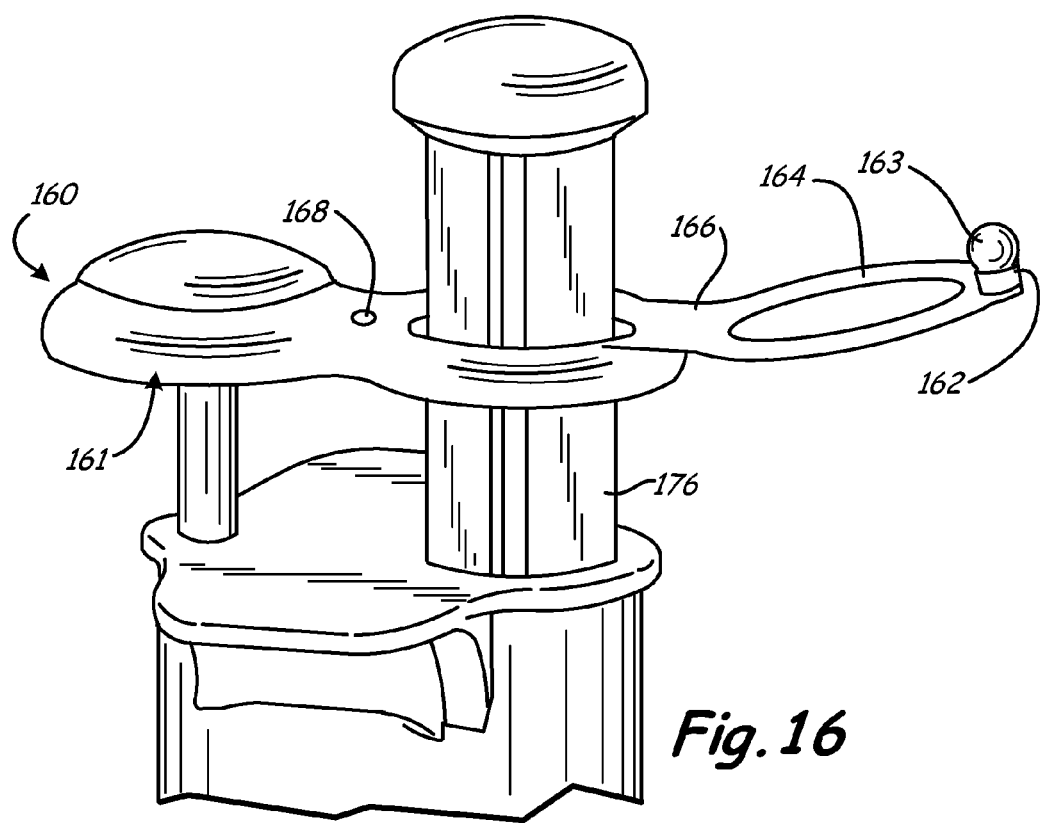
FIG. 16 is a partial exploded view of the syringe of FIG. 15.
Figure 17:
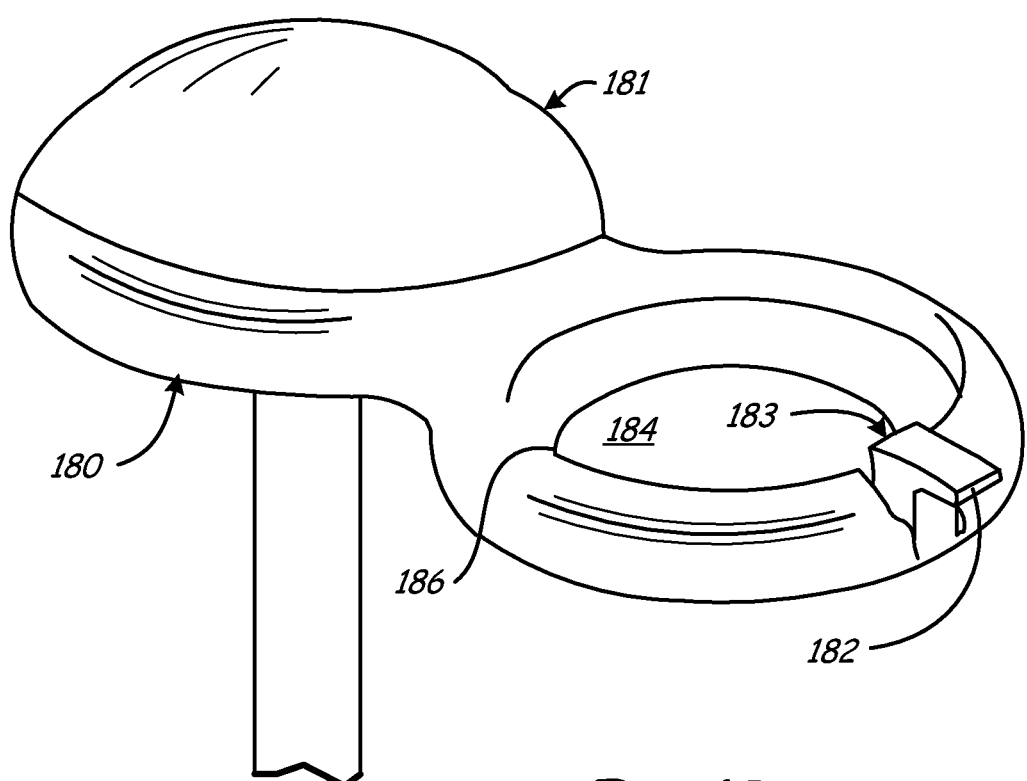
FIG. 17 is a perspective view of another plunger head.

FIGS. 15 and 16 include another configuration of a plunger head 160. The plunger head 160 operates similarly to the plunger head 130. However instead of utilizing two pegs 146 and 148 that engage side surface of the plunger 130, the plunger head 160 includes a single peg 162 extending from a distal end of a flap 164. The flap 164 is pivotally attached to a main body of the plunger head 160 with a hinge 166.

With the right plunger 170 positioned through a bottom aperture of the main body 161, the flap 164 is rotated such that the peg 162 is proximate a through bore 168 in the main body of the main body 161. The peg 162 has an end 163 that has a diameter that is slightly larger than a diameter of the through bore 168 such that when manual force is placed on the flap 164, the peg 162 is forced into the through bore 168 with the protruding end positioned below the bottom surface of the main body 161 of the plunger head 160 which secures the right plunger 170 to the main body of the plunger head 160.

Applying manual force in an opposite direction forces the peg 162 out of the through bore 168, such that the flap 164 can pivot about the hinge 166 to provide access to the right plunger head 170. With access to the right plunger head 170, the plungers can be manipulated independently from each other.

Figure 18:
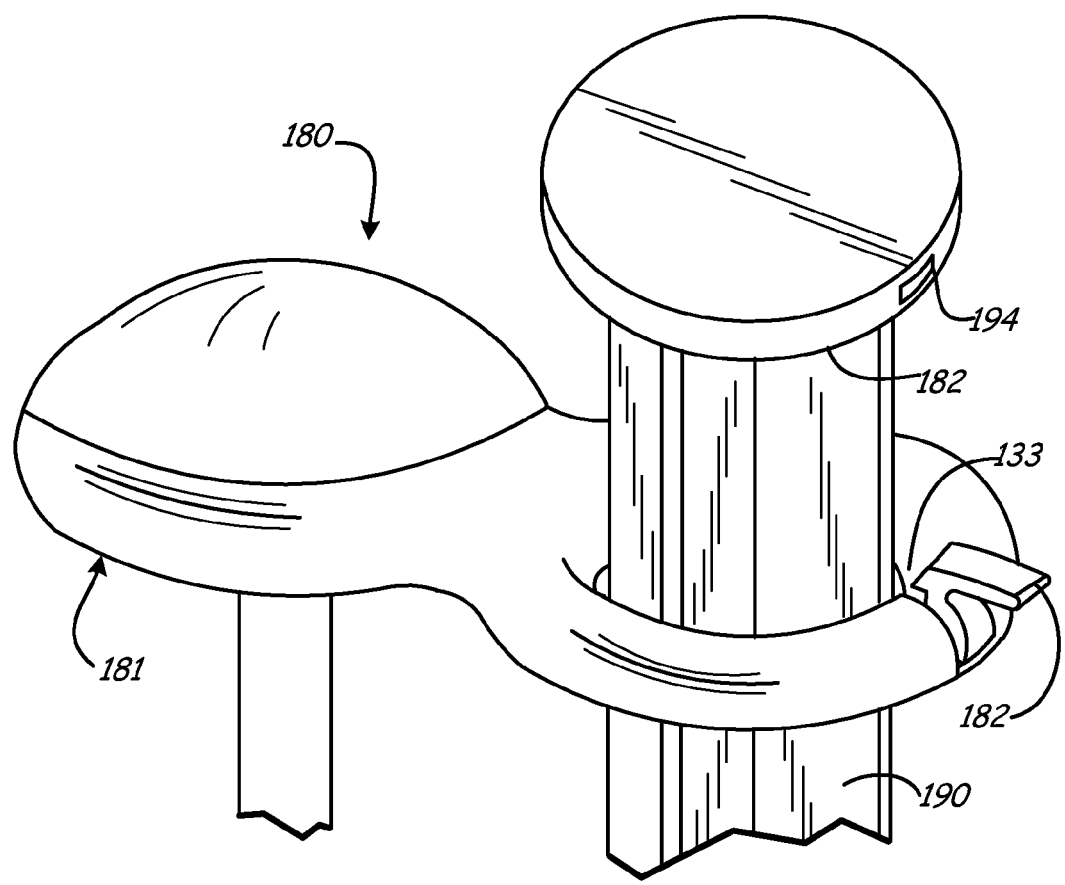
FIG. 18 is a partial exploded view of the plunger head of FIG. 17 with a partially removed plunger.
Figure 19:
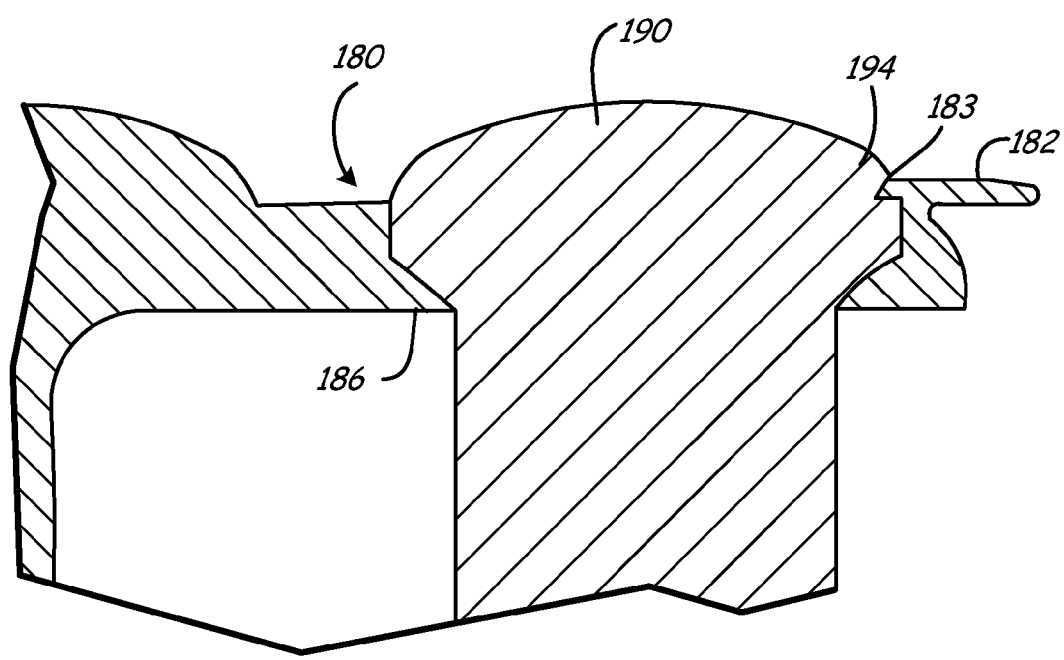
FIG. 19 is a sectional view of the plunger head of FIG. 17 with a plunger attached thereto.

Referring to FIGS. 18-20, another configuration of a plunger head 180 is illustrated. The plunger head 180 includes a main body 181 having an aperture 184 with a tapered bottom surface 186 that constricts the diameter of the aperture 184. The tapered bottom surface 186 engages a tapered surface of the plunger head 182 of the right plunger 190. The engagement of the tapered surfaces prevents the right plunger 190 from falling through the aperture 184 and disengaging the main body 181 of the plunger head 180.

The main body 181 includes a latch 182 that is pivotally attached to the plunger head 180. An end 183 of the latch 182 extends into the aperture 184 and is positionable within a notch 194 in the right plunger head 182. Positioning the end 183 of the latch 182 into the notch 194 secures the right plunger 190 to the main body 180. Applying manual force in an opposite direction removes the end 183 from the notch 194 which allows the right plunger 180 to move independently from the left plunger 181.

Each of the dual chamber syringes with the plunger heads 72, 74, 100, 130, 160 and 180 are designed to apply two liquids to a surgical site. Typical fluids applied are a blood component such as plasma and another liquid such as a hardener. However, the device 10 and the syringes with plunger heads 72, 74, 100, 130, 160 and 180 are not limited any two these particular liquids, but rather the device and syringes can be utilized to transfer any fluids from the non-sterile field to the sterile field in an operating room.

Typically, the blood is removed from the patient during the procedure in the sterile field in an operating room and taken to the non-sterile field in the operating room to separate components in the blood with a device such as a centrifuge. While in the non-sterile field, the blood components or blood are drawn into the right chamber 66 with the right plunger 70 where the right plunger 70 is operated independent from the left plunger 68. Independent operation of the plungers 68 and 70 allows for a precise amount of blood or blood component to be drawn into the right chamber 66.

With the precise amount of blood or blood component in the right chamber 66, the left plunger 68 is retracted to draw the gelling liquid or hardener into the left chamber 64. The exact ratio of the blood or blood component in the right chamber 66 to the gelling liquid or hardener in the left component is obtained when the head of the right plunger 70 can be secured to the head of the left plunger 68 as described in FIGS. 5-10, or the right plunger head is secured to the main body of the plunger head as described in FIGS. 11-19. Therefore, the dual syringe device provides for a leveling feature that allows for an optimum amount of both the blood or blood component and the gelling agent or hardener to be applied to the surgical site.

Once the dual chamber syringe 60 is filled with the selected amount of blood or blood component and hardener, the syringe is positioned into the cavity 30 of the mechanism 10 such that the discharge ends 78, 80 of the left and right chambers 64 and 66 are positioned within the left and right inlet ports 18 and 20 of the transfer device 10

The device 10 is then transferred proximate personnel in the sterile field who position a sterile dual chamber syringe into the left and right outlet ports 46 and 48 which are also in the sterile field. Simultaneously, the left and right plungers 68 and 70, which are connected by the plunger heads 72 and 74, are depressed and the left and right plungers of the sterile syringe are retracted to transfer the fluids from the non-sterile field to the sterile field while maintaining the sterility of the sterile field.

Once the fluids are transferred to the sterile syringe in the sterile filed, a sterile spray nozzle is attached to the discharge ends of the left and right chambers. The plunger heads are interconnected and depressed simultaneously such that the two fluids sprayed onto the surgical site at the optimal concentrations.

Although the present invention has been described with reference to preferred embodiments, workers skilled in the art will recognize that changes may be made in form and detail without departing from the spirit and scope of the invention.

What is claimed is:

1. A device for maintaining the sterility of a sterile field in a surgical environment when transferring liquid from a non-sterile field to the sterile field, the device comprising:
    a barrier wall comprising a first surface and a second surface separated from the first surface and a first through bore spaced apart from a second through bore, the first and second through bores extending from the first surface to the second surface;
    a first inlet port attached to the first surface of the barrier wall and in fluid communication with the first through bore; and
    a first outlet port attached to a second surface of the barrier wall and in fluid communication with the first inlet port and the first through bore, the first inlet port and the first outlet port both being configured to engage a discharge end of separate first and second syringes,
    wherein the discharge ends of the first and second syringes are configured to fluidly communicate respectively with the first inlet port and the first outlet port for transferring liquid from the non-sterile field of the first syringe to the sterile field of the second syringe without contaminating the sterile field.

2. The device of claim 1 and further comprising:
    a second inlet port spaced apart from the first inlet port and attached to the first surface of the barrier wall and in fluid communication with the second through bore; and
    a second outlet port spaced apart from the first outlet port and attached to the second surface of the barrier wall and in fluid communication with the second inlet port and the second through bore.

3. The device of claim 2 and further comprising:
    a continuous side wall extending from a perimeter of the barrier wall wherein a distal end of the continuous side wall extends above a top surface of both the first and second inlet ports.

4. The device of claim 3 and wherein the distal end of the continuous side wall forms an opening to a cavity defined by an interior surface of the side wall and the first surface of the barrier wall wherein the first and second inlet ports are within the cavity.

5. The device of claim 2 and wherein the continuous side wall includes slanted surfaces that aid in positioning the discharge ends of the first syringe within the first and second inlet ports.

6. The device of claim 2 and further comprising first and second cylinders attached to and extending from the second surface of the barrier wall and wherein the first outlet port is positioned within the first cylinder and the second outlet port is positioned within the second cylinder.

7. The device of claim 4 and wherein the first and second cylinders both include interior walls that form a frusto-conical cavity which aids in positioning discharge ends of syringes within the first and second discharge ports.

8. The device of claim 5 and further comprising a substantially flat plate extending from entrances to the frusto-conical cavities.

9. A kit for transferring fluids from a non-sterile field to a sterile field in an operating room, the kit comprising:
    a fluid transfer device comprising:
    a barrier wall comprising a first surface and a second surface separated from the first surface and a first through bore spaced apart from a second through bore, the first and second through bores extending from the first surface to the second surface;
    a first inlet port attached to the first surface of the barrier wall and in fluid communication with the first through bore;
    a first outlet port attached to a second surface of the barrier wall and in fluid communication with the first inlet port and the first through bore, the first inlet port and the first outlet port both being configured to engage a discharge end of separate syringes; and
    at least two syringes for engaging the device.

10. The kit of claim 9 and wherein the device further comprises:
    a second inlet port spaced apart from the first inlet port and attached to the first surface of the barrier wall and in fluid communication with the second through bore; and
    a second outlet port spaced apart from the first outlet port and attached to the second surface of the barrier wall and in fluid communication with the second inlet port and the second through bore.

11. The kit of claim 9 wherein at least one of the two syringes for engaging the device is a dual chamber syringe, the dual chamber syringe comprising:
    first and second syringe chambers; and
    first and second plungers respectively received for movement within the first and second syringe chambers;
    wherein the first and second plungers are selectively capable of being coupled together for simultaneous movement and further capable of being uncoupled from one another to allow independent movement of one of the first and second plungers relative to the other of the first and second plungers.

12. The kit of claim 11 wherein the dual chamber syringe further comprises:
    a securing mechanism movable between locked and unlocked positions relative to at least one of the first and second plungers, the securing mechanism facilitating the coupling and uncoupling of the first and second plungers relative to each other.

13. The kit of claim 12 wherein the securing mechanism of the dual chamber syringe further comprises:

first and second tabs respectively on the first and second plungers.

\* \* \* \* \*